United States Patent [19]

Wagner et al.

[11] Patent Number: 4,806,468

[45] Date of Patent: Feb. 21, 1989

[54] MEASUREMENT OF GLYCOSYLATED HEMOGLOBIN BY IMMUNOASSAY

[75] Inventors: Daniel B. Wagner, Raleigh; Ashoke Sinha, Durham, both of N.C.

[73] Assignee: Becton, Dickinson and Company, Franklin Lakes, N.J.

[21] Appl. No.: 11,663

[22] Filed: Feb. 5, 1987

[51] Int. Cl.$^4$ .................. G01N 53/00; G01N 33/72; G01N 1/00; C12Q 1/28

[52] U.S. Cl. ........................................ 435/7; 435/28; 435/68; 435/188; 435/810; 436/67; 436/175; 436/811

[58] Field of Search ................ 435/7, 28, 188, 810, 435/68; 436/66, 67, 175, 176, 811, 807, 808

[56] References Cited

U.S. PATENT DOCUMENTS 4,582,811  4/1986  Pucci et al. ..................... 436/548
4,695,552  9/1987  Schmitt et al. .................. 436/66
4,727,036  2/1988  Knowles et al. .................. 530/387

Primary Examiner—Esther M. Kepplinger
Assistant Examiner—Carol A. Spiegel
Attorney, Agent, or Firm—Richard E. Brown

[57] ABSTRACT

A method for determining glycosylated hemoglobin in a diluted blood sample includes binding of glycosylated hemoglobin to a specific monoclonal antibody and binding of nonglycosylated hemoglobin to a polyclonal antibody. The polyclonal antibody binds to all hemoglobin fractions and blocks the peroxidase activity thereof, except glycosylated hemoglobin bound to the monoclonal antibody which retains peroxidase activity. A beam of light having a wavelength of about 416 nm is passed through the assay medium and is absorbed by all hemoglobin fractions, bound or unbound, and this absorbance thereby provides a measure of total hemoglobin. Hydrogen peroxide and a peroxidase substrate are added. The substrate is oxidized by the peroxide to a product having an absorbance at a wavelength different from 416 nm, the oxidation being catalyzed by the retained peroxidase activity of the bound glycosylated hemoglobin. This absorbance provides a measure of glycosylated hemoglobin. From the two absorbances, the percentage of glycosylated hemoglobin in the total hemoglobin of the sample may be calculated. The invention includes a kit of materials useful in performing the assay method of the invention.

18 Claims, 4 Drawing Sheets

HM..... heme
AB...... antibody
: ...... binding

MEASUREMENT OF GLYCOSYLATED HEMOGLOBIN BY IMMUNOASSAY

BACKGROUND OF THE INVENTION

1. Field of the Invention

This invention relates to a method for assay of glycosylated hemoglobin, and more particularly, to a homogeneous method and materials for determination of the percentage of glycosylated hemoglobin in the total hemoglobin of a blood sample.

2. Background of the Invention

Hemoglobin (Hb) is a mixture of proteins consisting of a prosthetic heme group attached to two pairs of unlike polypeptide chains, and in this disclosure, Hb refers in general to this mixture. In the major component of the mixture, conventionally terme HbA, the chains are designated $\alpha$ and $\beta$. Total Hb, hereinafter termed Hbt, includes the major $\alpha_2$, $\beta_2$ fraction and several minor components having different chains, and various hemoglobin fractions formed by nonenzymatic glycosylation reactions of intact Hb molecules. As used in this disclosure, Hb and Hbt actually designate the same material. For clarity, Hbt is used to emphasize total hemoglobin, and Hb is used for general discussion which can apply to any hemoglobin fraction or combination of fractions.

The fractions of Hb are conventionally separated by chromatography. The main chromatographic fraction, making up about 90% of Hbt, is nonglycosylated and is generally referred to as HbA, and, in this disclosure, the term HbA is used to designate total nonglycosylated Hb. The major fraction of glycosylated Hb, conventionally and in this disclosure, is termed HbAlc.

HbAlc arises by reaction of a terminal valine amino group in the $\beta$ chain with the aldehyde group of glucose to give an unstable aldimine. Amadori rearrangement of the aldimine gives HbAlc, which is characterized by a $\beta$-ketoglycoside linked to the valine amine group.

The determination of HbAlc and the percentage thereof in Hbt is important in the diagnosis of diabetes mellitus and in monitoring the treatment of diabetic patients. In nondiabetic people, the HbAlc level is generally between 4-8% of Hbt. In diabetics, the HbAlc level is 2-3 fold higher and may range up to 20% of Hbt.

A variety of methods has been proposed for assessment of HbAlc and Hbt levels in a sample of a patient's blood. Early macrochromatographic separation methods have been supplanted by microchromatography methods using ion-exchange resins as column packing. U.S. Pat. Nos. 4,270,921 to Graas, 4,389,491 to Hanamoto, 4,436,820 to Reiter and 4,407,961 to Sanders are exemplary of HbAlc determinations using ion-exchange techniques.

Other disclosures achieve separation without ion-exchange. Electrophoretic separation is described in U.S. Pat. No. 4,351,711 to Ambler. Electrochromotographic separation is disclosed in U.S. Pat. No. 4,222,836 to Kerr. U.S. Pat. No. 4,269,605 to Dean discloses complexation of HbAlc with a dihydroxyboryl reagent. In this method, separation of the complex from other Hb fractions is carried out by physical means, such as by bonding the boryl reagent to a solid phase, so that HbA can be washed away.

All existing methods for determination of HbAlc involve separation of the HbAlc from Hbt prior to measurement. These separation steps entail repeated accurate pipetting steps and are costly, time-consuming, labor intensive procedures requiring skilled technicians. There is a definite need for a simple, rapid, accurate assay which can be performed by unskilled technicians. It is toward the fulfillment of this need that this invention is directed.

SUMMARY OF THE INVENTION

A method for determining HbAlc in a blood sample is based on the peroxidase activity of Hb.

A first portion of a diluted blood sample is contacted with a source of peroxide, and a peroxidase substrate. The peroxidase activity of Hb in the sample catalyzes oxidation of the substrate to a product by the peroxide. A beam of light having a wavelength within the absorption range of the product is passed through the assay medium. The extent of absorbance is a measure of Hbt in the sample.

A second portion of the blood sample is mixed under binding conditions with an antibody specific for Hb (hereinafter referred to as anti Hb) and an antibody specific for HbAlc (hereinafter referred to as anti HbAlc). After binding, the peroxide source and the peroxidase substrate are added. Bound HbAlc, but not bound HbA, retains its peroxidase activity. The retained peroxidase activity of the bound HbAlc catalyzes reaction of the peroxide and the substrate to give the product. The product absorbs the beam of light, the extent of absorbance providing a measure of HbAlc in the sample.

In a preferred embodiment of the invention, measurement of both Hbt and HbAlc may be carried out on the same blood sample. A mixture of the sample, diluted in phosphate buffered saline (PBS), a monoclonal anti HbAlc and a polyclonal anti Hb are incubated to cause binding, as described above. A beam of light having a wavelength maximum at 416 nm is passed through the mixture to give a first level of absorbance, the magnitude of which provides a measure of Hbt. The substrate and a source of peroxide are added. Peroxide from the source reacts with the substrate to give the product, the reaction being catalyzed by bound HbAlc which has retained its peroxidase activity. A second beam of light having a wavelength maximum within the absorption range of the product is passed through the mixture to give a second level of absorbance, the magnitude of which provides a measure of HbAlc.

Another aspect of the invention is a kit of materials useful in performing the method of the invention.

Thus, in accordance with the invention, materials useful for determining HbAlc by a simple method which takes advantage of the peroxidase activity of Hb is provided. The method is homogeneous, i.e., it may be performed without separating Hb fractions so that delicate assay operations, such as pipetting steps, are avoided. The assay may, therefore, be performed by unskilled technicians, and because simple, conventional and inexpensive equipment is used, may be performed in physician's offices, or even in the home.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The present invention is directed to a homogeneous method for determining the percentage of HbA1c in the Hbt of a blood sample. The method is based on the known peroxidase activity of Hb and on selective binding characteristics of Hb and HbA1c with specific antibodies.

Polyclonal anti Hb which binds to all Hb fractions, including all glycosylated Hb fractions, is known. Monoclonal anti HbA1c which binds specifically to HbA1c is known and is described in U.S. Pat. No. 4,478,744 to Mezei.

In accordance with the present invention, it has been found that the peroxidase activity of Hb is blocked when the Hb binds to anti Hb. On the other hand, peroxidase activity of HbA1c is retained when it binds to anti HbA1c.

Figure 1:
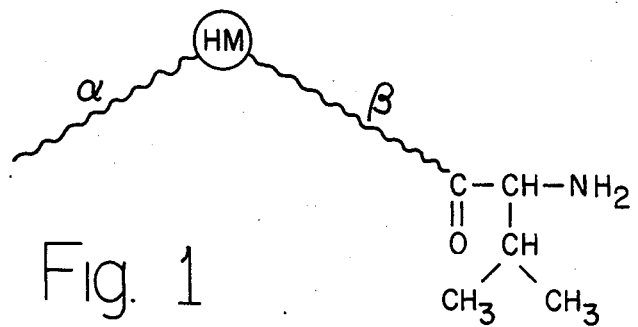
FIG. 1 is a partial structural illustration of a Hb molecule.
Figure 2:
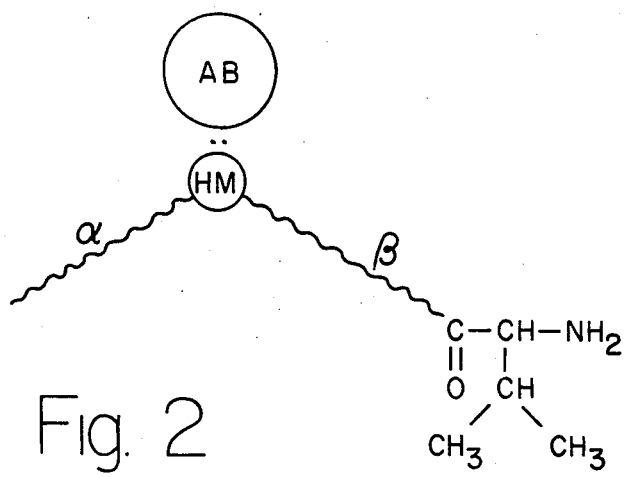
FIG. 2 is a partial structural illustration of a complex of the Hb molecule of FIG. 1 and an antibody.

It is generally believed that the peroxidase activity of Hb is associated with the heme group. FIG. 1 shows an Hb molecule having an chain and a B chain terminating in a valine group having a free amino group, and FIG. 2 illustrates binding of anti Hb to the heme group.

Figure 3:
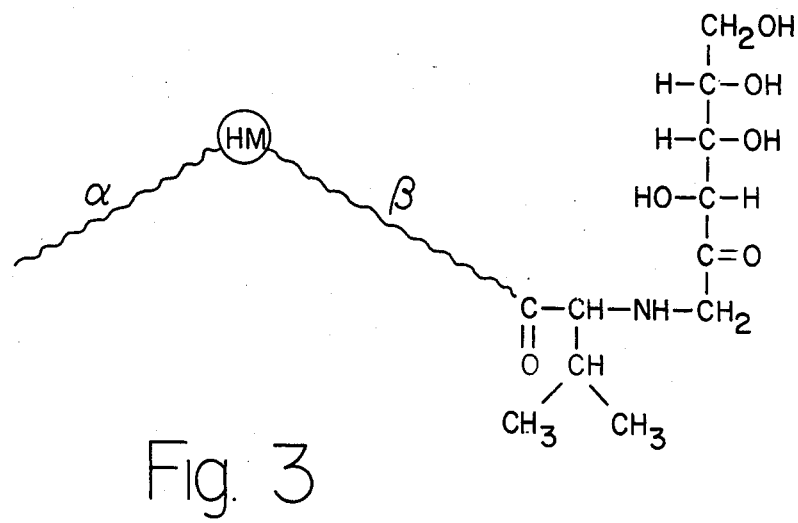
FIG. 3 is a partial structural illustration of an HbAlc molecule.
Figure 4:
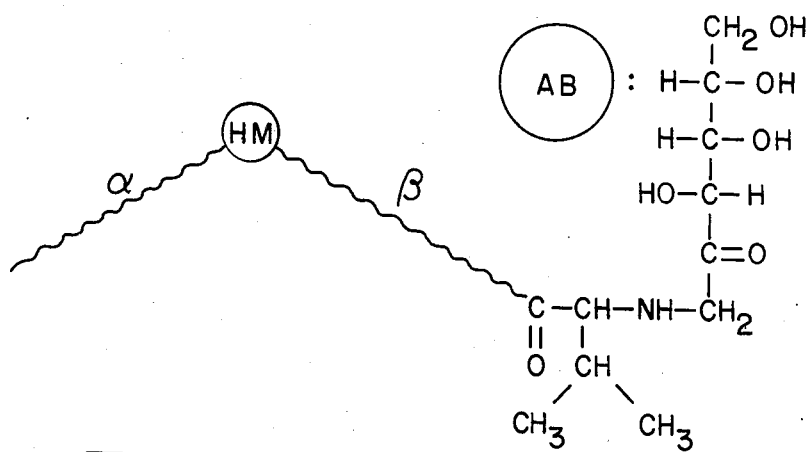
FIGS. 4 and 5 are partial structural illustrations of a complex of the HbA1c molecule of FIG. 3 and an antibody.

FIG. 3 shows the β-ketoglycoside structure resulting from reaction of the valine amino group with glucose and Amadori rearrangement of the intermediate aldimine (not shown). Binding of an antibody to the glycoside portion of HbA1c is illustrated in FIG. 4.

If a bound complex of HbA1c and anti HbA1c is contacted under binding conditions with anti Hb, no further binding takes place, i.e., the binding of anti HbA1c to the glycoside portion of HbA1c inhibits binding of anti Hb to the heme portion of the complex. Thus, HbA1c does not bind to both antibodies simultaneously. Further, when a mixture of HbA and HbA1c, as for example, a blood sample, is contacted under binding conditions with both anti Hb and anti HbA1c, no anti Hb:HbA1c complex forms, even though HbA1c binds readily to anti Hb in the absence of anti HbA1c.

Figure 5:
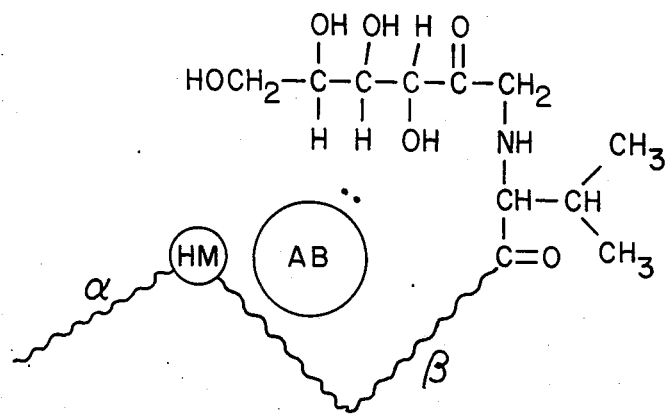

It is believed, but as yet unsubstantiated, that the inability of the anti HbA1c:HbA1c complex to bind anti Hb, even though its heme portion is unbound, is due to steric hindrance consequent to the flexibility of the β chain. FIG. 5 illustrates anti HbA1c positioned proximate to, but not bound to, the heme portion whereby anti Hb is prevented from binding.

The above observations are used in the present invention in a homogeneous method to determine the concentration of HbA1c in a blood sample, or, preferably to determine the percentage of HbA1c in the Hbt of a blood sample.

A blood sample containing an unknown percentage of HbA1c to be determined is diluted with an appropriate diluent, which may serve as the assay vehicle. Any diluent may be used which does not interfere in any way with the subsequent binding reactions or peroxidase-catalyzed reactions. Suitable diluents are, for example, tris(hydroxymethyl)aminomethane(TRIS), N-2-hydroxyethylpiperizine-N'-2-ethanesulfonic acid(-HEPES) and, preferably phosphate buffered saline (PBS). The ratio of blood to the diluent is not critical, and advantageously may be from about one part by volume of blood to about 500 to 1500 parts of diluent. A preferred ratio of blood to diluent may be from about 1:800 to 1:1200.

Prior to binding, the red blood cells in the sample may be lysed to release the Hb. When a blood sample is diluted with PBS as described above, the cells undergo spontaneous lysis. If desired, the lysis may be accelerated by addition of an exogenous lysing agent. Exemplary of suitable lysing agents are, for example, surfactants, such as the polyoxyethylenesorbitan esters. Lysis of red blood cells is conventional and no further details in this respect are necessary.

A mixture of anti Hb and anti HbA1c in PBS or other suitable diluent is added to the solution of lysed red blood cells. A large excess of both antibodies may be added to ensure that all the HbA1c and HbA bind to the appropriate antibody. The antibodies may preferably be added as a solution of about 4 to 15 mg of antibody per ml in the same diluent as used for the blood, and may be either monoclonal or polyclonal. Preferably, anti Hb is polyclonal and anti HbA1c is monoclonal.

If desired, the mixture may be incubated to ensure binding. Any suitable time and temperature may be used for the incubation. It is preferred to incubate the mixture for about 10 to 15 minutes at about 25° to 35° C.

A beam of light having a wavelength maximum about 410–420 nm, preferably 416 nm, or about 535–545 nm, preferably 540 nm, is passed through the mixture and is absorbed by the Hbt in the sample. All Hb, whether free or glycosylated, bound or unbound, absorbs light of these wavelengths. Measurement of the absorbance thus provides a measure of Hbt in the blood sample. Since binding to the antibodies does not affect this absorbance, the light beam at about 416 nm or about 540 nm may be passed through the assay at any time prior to, during or subsequent to binding or incubation.

Subsequent to measurement of Hbt, a peroxidase substrate and a solution of hydrogen peroxide in a suitable solvent, such as water or the diluent described above are added. Under catalysis by the retained peroxidase activity of the bound HbA1c, the peroxide oxidizes the substrate to a detectable product.

Any substrate may be used which undergoes peroxidase-catalyzed oxidation with peroxide to a product which absorbs light, preferably in the visible range, of a wavelength different from that of the other assay components. Exemplary of, but not limited to, suitable substrates are 2,7-diaminofluorene, 3,5-diaminobenzidine, 2,2'-azinobis(3-ethylbenzothiazoline-6-sulfonic acid diammonium salt and, preferably, leuco malachite green (LMG). In the presence of a peroxidase, the substrate is oxidized by the peroxide to the product. When the substrate is LMG, the product is malachite green.

In alternative embodiments of the invention, an organic peroxide, such as benzoyl peroxide, or a peroxide precursor may be added. The precursor may be any substance which releases peroxide into the assay vehicle. Peroxide release from the precursor may be initiated by a separate reagent added for the purpose, or, preferably is consequent to contact of the precursor with the assay vehicle. Exemplary of, but not limited to, suitable precursors are inorganic peroxide salts and a mixture of glucose and glucose oxidase. The preferred precursor is a salt of metaperboric acid, such as sodium metaperborate, which, in the presence of water, is converted to boric acid with liberation of peroxide.

A second beam of light having an absorption maximum within the absorbance range of the product is passed through the mixture. The range of absorbance of malachite green is from about 610 to 630 nm, with the maximum at about 620 nm. Since only bound HbAlc retains peroxide activity, measurement of the absorbance within this range, preferably at 620 nm, provides a measure of HbAlc in the blood sample. The percentage of HbAlc in Hbt may then easily be calculated by the simple formula:

$$\frac{[HbAlc]}{[Hbt]} \times 100$$

wherein [HbAlc] and [Hbt] represent the concentrations of HbAlc and Hbt respectively. The value of [HbAlc] may be obtained from a standard curve using the absorbance value obtained at 620 nm and the value of [Hbt] may be obtained from a second standard curve using the absorbance at 416 nm.

It is evident that other substrates may be used which undergo oxidation to products which absorb light over different wavelength ranges, and the wavelength of the second beam of light may be chosen to correspond to the absorbance range of the expected product. For example, if 2,7-diaminofluorene is used as the substrate, the product will absorb from about 570 to 620 nm.

In another embodiment of the invention, HbAlc may be determined as above, and Hbt may be determined with a second portion of the blood sample treated with precursor and substrate but without the two antibodies. Absent the antibodies, all Hb fractions in the sample remain unbound and, therefore, retain their peroxidase activity. Thus, when the substrate is LMG, absorption at 620 nm with this second portion of the sample provides a measurement of Hbt.

Any suitable instrument may be used to provide incident light and detect absorbance thereof. Preferred instruments are simple photometers. For example, in the preferred embodiment of the invention wherein absorbance at both 416 nm and 620 nm is measured, a photometer having two diodes is advantageously used. In the embodiment of the method using two portions of the sample wherein absorbance at only 620 nm provides measurement of both Hbt and HbAlc, a single-diode photometer may be used. Selection of an appropriate instrument is well within the purview of one skilled in the art.

It is readily seen that the magnitude of light absorbance by the product is proportional to the concentration of the product in the mixture, and that the concentration of product in turn is determined by the rate at which the substrate is converted to product. Thus, measurement of the absorbance may be made under either kinetic or end-point conditions. Kinetic measurements determine the rate of increase in absorbance which occurs over a period of time, and are generally carried out by making a series of measurements at various times after combining the assay reagents. End-point measurements determine the extent of absorbance at a given time after the assay reagents have been combined.

Another aspect of the invention is a kit of materials useful in performing the method of the invention. The kit may contain premeasured quantities of the two antibodies and the substrate. The antibodies may preferably be provided as a solution in a suitable diluent, to serve as the assay vehicle, and the solution may be supplied in an appropriate container to serve as the assay reaction vessel.

The substrate may be supplied in solid form or in solution in a diluent, preferably the same diluent as used for the antibodies. When supplied in solid form, the substrate may be provided as tablets or as a capsule coated with a dissolvable material, such as salt or gelatin. The capsule may be added to the assay vehicle containing the antibodies concurrently with the blood sample, and is adapted to dissolve and release the precursor and substrate subsequently to the binding reactions. For example, the capsule may be affixed within a cap for the assay vessel so that when the sample and antibodies are combined in the assay vehicle and the cap affixed to the vessel, the capsules contact the vehicle. The coating is predetermined to dissolve subsequent to completion of the binding reactions and thereby release the substrate.

The kit may also include a peroxide precursor, hydrogen peroxide, solutions containing known concentrations of Hb and HbAlc and a solution devoid of Hb and HbAlc to serve as a negative control. Other solutions and utensils such as saline, buffers, diluents, vials, droppers and the like useful in performing the assay may also be provided.

The following examples are provided to further describe the invention.

EXAMPLE I

A blood sample was diluted with 1000 parts by volume of PBS (a mixture 0.01M mono- and disodium phosphate in 0.15M sodium chloride) and 50 $\mu l$ were placed in each of two tubes. To tube A were added 20 $\mu l$ of a 5 mg/ml solution of polyclonal anti Hb in PBS, an to tube B were added 20 $\mu l$ of PBS. The tubes were incubated for 10 minutes at room temperature. A developing solution consisting of two drops of 3% peroxide and one drop of $1 \times 10^{-3}M$ LMG in 95% acetic acid was added to each tube. The solution in tube A remained colorless while that in tube B turned green, showing that the anti Hb added to tube A blocked the peroxidase activity of the Hb in the blood sample.

EXAMPLE II

The experiment of Example I was repeated except purified HbAlc was used instead of the blood sample in both tubes A and B. As in Example I, tube A remained colorless and tube B developed color, showing that glycosylated Hb has peroxidase activity and that this activity is blocked by anti Hb.

EXAMPLE III

Example II was repeated except purified HbA was used in place of purified HbAlc. As in Example I and II, tube A remained colorless while tube B developed color, showng that purified non-glycosylated Hb has peroxidase activity which is blocked by anti Hb.

EXAMPLE IV

Fifty $\mu l$ of the blood sample-PBS solution of Example I was placed in each of two tubes. Tube A received 50 $\mu l$ of a 2.15 mg/ml solution of monoclonal anti HbAlc in PBS and tube B received 50 $\mu l$ of PBS. After incubation, both tubes received 50 μl of the polyclonal anti Hb solution of Example I. The tubes were incubated again and treated with the developing solution of Example I. Tube A developed color while tube B remained colorless showing that the peroxidase activity of HbAlc in tube A was protected by binding to anti HbAlc while the peroxidase activity of HbAlc in tube B, absent anti HbAlc, was blocked by the anti Hb.

EXAMPLE V

Monoclonal anti HbAlc in 0.05M sodium carbonate buffer solution was added to the wells of a polystyrene microtiter plate, and the plate was incubated overnight at room temperature to cause absorption of the antibody onto the plate. Unfilled binding sites in the wells were filled by incubating the plate with 5% bovine serum albumin in the conventional way and the plate was rinsed.

To well A was added 200 μl of a 1:1000 dilution of purified HbAlc in PBS, and to well B was added a 1:1000 dilution of Hb in PBS. The wells were incubated overnight at room temperature, rinsed and treated with developing solution. Well A developed color while well B remained colorless, showing that the peroxidase activity of HbAlc in well A was retained after binding to anti HbAlc but blocked after binding to anti Hb in tube B.

EXAMPLE VI

Twenty-five μl of a 1000:1 dilution of purified HbAlc in PBS were added to each of three tubes. Tube A received 50 μl of monoclonal anti HbAlc in PBS. The mixture was incubated for 15 minutes at room temperature, treated with 50 μl of polyclonal anti Hb and incubated again. Developing solution was added and color developed in the mixture.

Tube B received 50 μl each of anti HbAlc and anti Hb. After incubation, developing solution was added and color was observed in the mixture. Tube C received 50 μl of polyclonal anti Hb. After incubation, developing solution was added. No color developed in the tube.

Tubes A and B show that the peroxidase activity of HbAlc was protected by binding to anti HbAlc in the presence of anti Hb, even when the two antibodies are added simultaneously. Tube C shows that, absent anti HbAlc, peroxidase activity of HbAlc is not protected.

EXAMPLE VII

Fifty μl of anti HbAlc were added to tube A and 50 μl of anti Hb were added to tube B. Developing solution was added to both tubes. No color developed in either tube.

This was a control experiment demonstrating that the antibodies do not possess any peroxidase activity.

EXAMPLE VIII

A solution (25 μl) of purified HbA was mixed with 50 μl of anti HbAlc, incubated for 15 minutes, then treated with 50 μl of anti Hb. Developing solution was added, but no color developed in the mixture.

This experiment shows that purified, unglycosylated Hb does not bind to anti HbAlc. Its peroxidase activity is, therefore, not protected, and when anti Hb is added, binding does take place with blocking of peroxidase activity.

EXAMPLE IX

Two hundred μl of two samples containing 15% and 10% HbAlc (and the remaining unglycosylated hemoglobin) were separately incubated with 200 μl of antiHbAlc for 15 minutes and then with 300 μl of antiHb for 10 minutes at room temperature. Developing solution (300 μl) was added to each, and the absorbances at 620 nm were followed. The absorbance values for 15% and 10% HbAlc solutions were 0.24 and 0.22, respectively.

This experiment shows that the method is capable of quantitatively differentiating between clinically important levels of glycosylated hemoglobin in the blood solution.

Thus, the invention includes a method and materials for determining glycosylated hemoglobin based on selective binding of two antibodies for glycosylated hemoglobin and nonglycosylated hemoglobin respectively. The method is homogeneous and thus entails no separation step and no tedious pipetting steps as required in prior art methods.

What is claimed is:

1. A method for determining the percentage of glycosylated hemoglobin fraction HbAlc in the total hemoglobin for a blood sample comprising:
   (a) preparing a mixture by contacting a blood smaple in a diluent with a monoclonal antibody specific for the glycoside portion of HbAlc and an antibody specific for the here portion of total hemoglobin whereby HbAlc in said sample binds to said monoclonal antibody to give a first bound fraction and nonglycosylated hemoglobin in said sample binds to said antibody to give a second bound fraction;
   (b) passing a first beam of light having a wavelength maximum of about 416 nm through said mixture, whereby said first and second bound fractions absorb said ligth to give a first absorbance due to said total hemoglobin;
   (c) measuring said first absorbance;
   (d) adding to said mixture a source of peroxide and a peroxidase substrate whereby peroxide from said source reacts with said substrate to give a product, said reaction being catalyzed by HbAlc in said first bound fraction but not by nonglycosylated hemoglobin in said second bound fraction;
   (e) passing a second beam of light through said mixture, said second beam having a wavelength maximum whereby it is absorbed by said product to give a second absorbance due to said HbAlc;
   (f) measuring said second absorbance; and
   (g) determining the percentage of HbAlc in said blood sample from the magnitude of said first and second abosrbances.

2. The method in accordance with claim 1 wherein said antibody specific for the heme portion of total hemoglobin is selected from the group consisting of a monoclonal antibody and a polyclonal antibody.

3. The method in accordance with claim 1 wherein said monoclonal antibody and said antibody are added sequentially with intervening and following incubation periods.

4. The method in accordance with claim 1 wherein said monoclonal antibody and said antibody are added simultaneously to said blood sample followed by an incubation period.

5. The method in accordance with claim 1 wherein said source of peroxide is selected from the group consisting of hydrogen peroxide, an organic peroxide and a peroxide precursor.

6. The method in accordance with claim 5 wherein said peroxide precursor is selected from the group consisting of metaperborate, an inorganic peroxide and a mixture of glucose and glucose oxidase.

7. The method in accordance with claim 1 wherein said substrate is selected from the group consisting of 2,7-diaminofluorene, leuco malachite green, 3,5-diaminobenzidine and 2,2'-azinobis(3-ethylbenzothiazoline-6-sulfonic acid diammonium salt.

8. The method in accordance with claim 1 further comprising adding a lysing agent to said mixture subsequent to said contacting.

9. The method in accordance with claim 8 wherein said lysing agent is a surfactant.

10. A method for determining the percentage of glycosylated hemoglobin fraction HbAlc in the total hemoglobin of a blood sample comprising:
 (a) preparing a first mixture by contacting a first portion of a blood sample in a diluent with a source of peroxide and a first increment of a peroxidase substrate whereby said peroxide reacts with said substrate to give a first increment of a product, said reaction being catalyzed by the total hemoglobin in said sample;
 (b) passing a first beam of light through said first mixture, said first beam having a wavelength maximum whereby it is absorbed by said first increment of product to give a first absorbance due to said total hemoglobin in said sample;
 (c) measuring said first absorbance,
 (d) preparing a second mixture by contacting a second portion of said blood sample in said diluent with a first antibody specific for HbAlc and a second antibody specified for the here portion of total hemoglobin whereby HbAlc in said sample binds to said first antibody to give a bound fraction and nonglycosylated hemoglobin in said sample binds to said second antibody to give a second found fraction;
 (e) adding to said second mixture a source of peroxide and a second increment of said peroxidase substrate whereby said peroxide reacts with said second increment of substrate to give a second increment of said product, said reaction being catalyzed by said HbAlc in said first bound fraction but not by nonglycosylated hemoglobin in said second bound fraction;
 (f) passing a second beam of light through said second mixture, said second beam having a wavelength maximum whereby it is absorbed by said second increment of product to give a second absorbance due to said HbAlc in said sample;
 (g) measuring said second absorbance; and
 (h) determining the percentage of said HbAlc in said blood sample from the magnitude of said first and second absorbances.

11. The method in accordance with claim 10 wherein said source is hydrogen peroxide.

12. The method in accordance with claim 10 wherein said source is a hydrogen peroxide precursor.

13. The method in accordance with claim 10 wherein said first antibody is monoclonal and said second antibody is polyclonal.

14. A method for determining the percentage of glycosylated hemoglobin fraction HbAlc in the total hemoglobin of a blood sample comprising:
 (a) preparing a mixture by contacting a blood smaple in phosphate buffered saline with a monclonal antibody specific for HbAlc and a polyclonal antibody specific for the heme portion of total hemoglobin whereby HbAlc in said sample binds to said monoclonal antibody to give a first bound faction and nonglycosylated hemoglobin in said sample binds to said polyclonal antibody to give a second bound fraction;
 (b) passing a first beam of light having a wavelength maximum of about 416 nm through said mixture, whereby said first and second bound fractions absorb said light to give a first absorbance due to said total hemoglobin;
 (c) measuring said first absorbance;
 (d) adding to said mixture hydrogen peroxide and leuco malachite green whereby said peroxide reacts with said leuco malachite green to give malachite green said reaction being catalyzed by HbAlc in said first bound fraction but not by nonglycosylated hemoglobin in said second bound fraction;
 (e) passing a second beam of light having a wavelength maximum of about 620 nm through said mixture, said second beam being absorbed by said malachite green to give a second absorbance due to said HbAlc;
 (f) measuring said second absorbance; and
 (g) determining the percentage of HbAlc in said blood sample from the magnitude of said first and second absorbances.

15. A kit for determining the percentages of glycosylated hemoglobin fraction HbAlc in the total hemoglobin of a blood sample comprising a first antibody which specifically binds to HbAlc, a second antibody which specifically binds to nonglycosylated hemoglobin, a source of peroxide, a peroxidase substrate and one or more containers, said HbAlc, afte binding to said first antibody, catalyzing a reaction of said peroxide and said substrate to a product.

16. The kit in accordance with claim 15 wherein said first antibody is monoclonal and said second antibody is polyclonal.

17. The kit in accordance with claim 15 wherein said source is selected from the group consisting of hydrogen peroxide, an organic peroxide and a hydrogen peroxide precursor.

18. The kit in accordance with claim 15 further comprising a solution useful in performing an assay method of the invention selected from the group consisting of saline, buffer, diluent and solution of an assay component.

* * * * *